United States Patent [19]

Blair

[11] 4,158,959
[45] Jun. 26, 1979

[54] APPARATUS FOR MEASURING THE PHYSICAL PROPERTIES OF MATERIAL

[75] Inventor: Raymond D. Blair, Houston, Tex.
[73] Assignee: Camco, Incorporated, Houston, Tex.
[21] Appl. No.: 882,714
[22] Filed: Mar. 2, 1978
[51] Int. Cl.² ............................................. G01N 9/00
[52] U.S. Cl. ...................................... 73/30; 73/32 A
[58] Field of Search .................... 73/30, 32 A; 310/25

[56] References Cited

U.S. PATENT DOCUMENTS

| | | | |
|---|---|---|---|
| 2,152,955 | 4/1939 | Coyne | 310/25 X |
| 3,223,861 | 12/1965 | Steiner | 310/25 X |
| 3,420,092 | 1/1969 | Dorsch | 73/30 X |

FOREIGN PATENT DOCUMENTS 524106 10/1976 U.S.S.R. .................................. 73/32 A

Primary Examiner—James J. Gill
Attorney, Agent, or Firm—Fulbright & Jaworski

[57] ABSTRACT

An apparatus for measuring the physical properties of material in which the sensing means is a tubular sensing member having a longitudial slot extending from one end to the other end. A support connected to the tubular member approximately midway between the ends of the tubular member and diametrically opposed to the slot. Electrical coil means extend longitudinally through the inside of and around the outside perimeter of the tubular member one or more times. An electrical driving circuit is connected to the coil means for vibrating the sensing member and an electrical sensing circuit is connected to the coil means for measuring the vibration of the sensing member.

1 Claim, 3 Drawing Figures

4,158,959

APPARATUS FOR MEASURING THE PHYSICAL PROPERTIES OF MATERIAL

BACKGROUND OF THE INVENTION

The present invention is directed to an apparatus for determining physical properties of materials such as density, specific gravity or other fluid properties. The measurement of physical properties, such as density, have been measured in the past by the use of a vibrating sensing element which is electrically vibrated and placed in contact with the material to be measured, and the vibration of the sensing element is measured for determining the effect of the material on the vibrating sensing element which is a measurement of a particular physical property of the material.

The present invention is directed to an improved sensing element for accurately measuring a fluid property of a material, and in particular the density of gas.

SUMMARY

The present invention is directed to an apparatus for measuring a physical characteristic of a material by an improved sensing element which is vibrated, and the vibration of the sensing element is measured whereby the change in vibration caused by the material is an indication of a physical characteristic being measured.

A further object of the present invention is the provision of an improved sensing element which is a tubular member having a longitudinal slot extending from one end to the other end. A support is preferably connected to the tubular member approximately midway between the ends of the tubular member and diametrically opposed to the slot.

Yet a still further object of the present invention is the provision of an apparatus for measuring a physical property of a material by the provision of such a tubular sensing member in which electrical coil means extend longitudinally through the inside and around the outside perimeter of the tubular member one or more times. An electrical driving circuit is connected to the coil means for vibrating the sensing member and an electrical sensing circuit is connected to the coil means for measuring the vibration of the sensing member.

Other and further objects, features and advantages will be apparent from the following description of a presently preferred embodiment of the invention, given for the purpose of disclosure and taken in conjunction with the accompanying drawings.

DESCRIPTION OF THE PREFERRED EMBODIMENT

Figure 1:
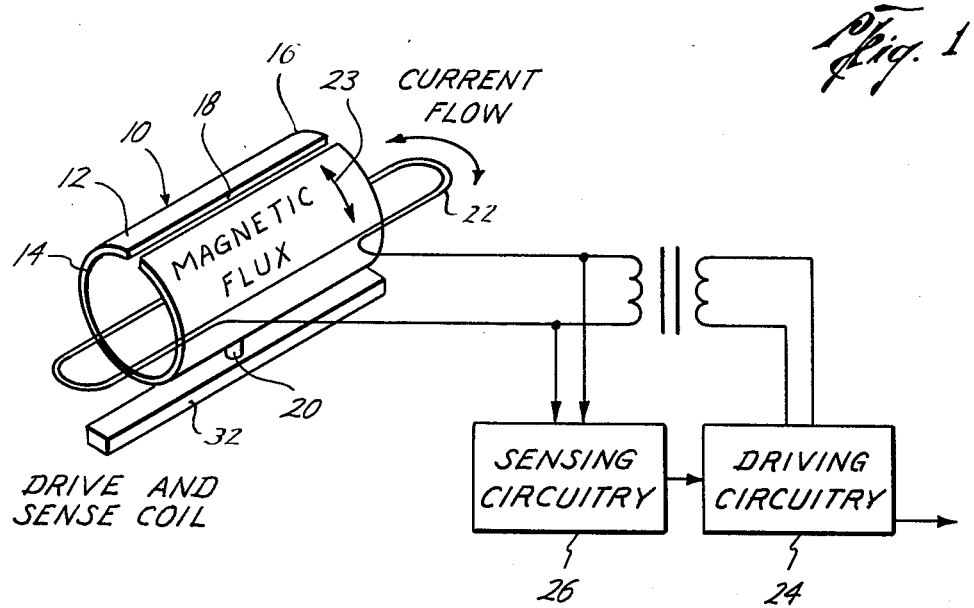
FIG. 1 is a schematic of the apparatus of the present invention.

Referring now to the drawings, particularly to FIG. 1, the reference numeral 10 generally indicates the sensing element of the present invention which includes a tubular member 12 having a first end 14 and a second end 16 and a longitudinal slot 18 extending from the first end 14 to the second end 16. The tubular member 12 is supported by a support 20 which is preferably connected to the body 12 approximately midway between the ends 14 and 16 and diametrically opposed to the longitudinal slot 18. As an example, the sensing element 10 may be made out of a nickel alloy with a high magnetic permeability such as the material sold under the trademark Ni-Span-C, and in which the tubular member 12 has an outside diameter of 0.5 inches, a wall thickness of 0.015 inches, is 1 inch long, and the slot 18 has a thickness of 0.005 inches.

The sensing element 10 is vibrated, placed in contact with the material to be measured, and the vibration of the element 10 is measured which provides an indication of a physical characteristic of the material being measured. The vibrating sensing element 10 may be vibrated at various frequencies and measurement may be made of various types of vibrations, such as the amplitude of vibration or the frequency of vibration. However, in the preferred embodiment, the sensing element 10 is vibrated at its resonant frequency and is vibrated at the resonant frequency continuously whereby the change in the measured resonant frequency is an indication of the physical characteristic of the material being measured. While any suitable driving and sensing circuit may be utilized, it is preferred to vibrate the sensing element 10 by a coil 22 of wire extending longitudinally through the inside of and around the outside perimeter of the tubular member 12, but without touching the member 12. For example, thirty-six turns of No. 26 wire has been found to be satisfactory. A driving circuit 24 is connected to the coil 22 and as electrical current passes through the coil 22, it magnetizes the member 12 creating magnetic lines of force 23 which follow the circumference along the entire length of the member 12. The magnetic force acts to shorten the magnetic path by closing the slot 18. An alternating current is applied to the coil 22, and the slot 18 decreases with each current peak regardless of polarity, causing the element 12 to vibrate at twice the applied frequency. As the applied frequency approaches one-half of the fundamental mechanical resonance or some subharmonic of that frequency, the amplitude of mechanical oscillations greatly increase.

In the preferred embodiment, since frequency is to be metered as a function of a physical characteristic such as density, it is desirable to drive the sensing element 12 at resonance continuously. The vibration of member 12 is measured by a suitable sensing circuit 26 connected to the coil 22. For example, a positive feedback system may be utilized in which the vibration of the element 12 is detected by the sensing circuit 26, amplified, and used to actuate the driving circuit 24. As long as the open loop gain is greater than unity, the oscillation of the sensing element 12 will be the frequency of maximum mechanical amplitude, that is, mechanical resonance. While simultaneous sensing and driving of the element 12 may be used, it is preferred to alternate the driving circuit 24 and sensing circuit 26 to avoid interference between driving and pickup signals.

Figure 2:
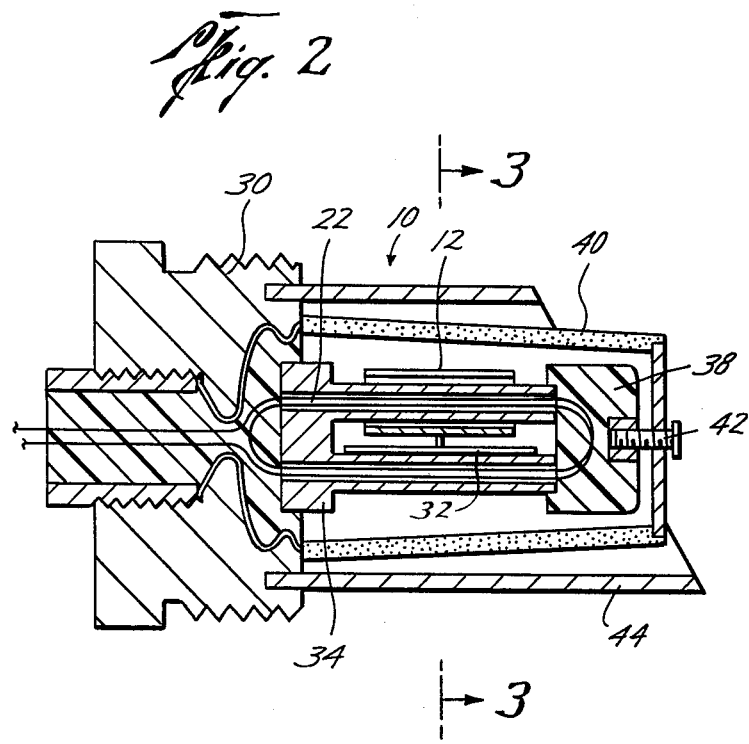
FIG. 2 is an elevational view, in cross section, of one embodiment of the sensing element of the present invention.

Referring now to FIG. 2, the mechanical structure of a suitable sensing element 10 is shown. The tubular sensing member 12 is shown supported from a pipe plug 30 for insertion into a pipe for measuring a physical characteristic, such as density, of a fluid material, such as gas, flowing through the pipeline (not shown). The support rod 20 may be connected to a bar 32 which in turn is connected to a support 34 which may include brass rods 36 for reenforcement and a cap 38 and be of a thermo-setting epoxy. The support 32 is bonded to the plug 30. The coil 22 extends through the pipe plug 30 for connection to the driving circuit 24 and sensing circuit 26. Preferably, a sintered bronze filter 40, 60-100 microns, which has been electrolessly nickelplated, is connected to the support 36 by a screw 42 for protecting the sensing member 10 from particle contamination. Also preferably a stainless steel shield 44 protects the sensing element 10 and filter 40 from wax buildup, direct impingement of flow, and water which may be traveling along the inside surface of the pipeline.

Figure 3:
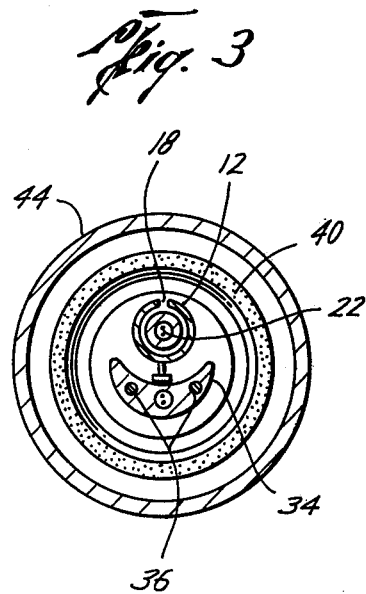
FIG. 3 is a cross-sectional view taken along the line 3—3 of FIG. 2.

In use, the structure illustrated in FIGS. 2 and 3 may be inserted into a pipeline and the driving circuit 24 vibrates the sensing element 10 at its resonant frequency in presence of the material, such as gas, to be measured. The physical property of the gas that is to be measured, such as density, will cause a change in the resonant frequency of the sensing element 10 and the vibration of the sensing element 10 is measured by the sensing circuit 26 which is an indication of the physical characteristic, such as density, being measured.

The present invention, therefore, is well adapted to carry out the objects and attain the ends and advantages mentioned as well as others inherent therein. While a presently preferred embodiment of the invention is given for the purpose of disclosure, numerous changes in the details of construction and arrangement of parts will be readily apparent to those skilled in the art and which are encompassed within the spirit of the invention and the scope of the appended claims.

What is claimed is:

1. An apparatus for measuring the physical properties of material comprising,
   a straight ferromagnetic tubular sensing member having a single longitudinal slot extending from one end to the other end,
   a support rod connected to said tubular member approximately midway between the ends of the tubular member and diametrically opposed to the slot,
   electrical coil means extending longitudinally through the inside of and around the outside perimeter of the tubular member one or more times,
   an electrical driving circuit connected to said coil means for vibrating said sensing member, and
   an electrical sensing circuit connected to said coil means for measuring the vibration of the sensing member.